United States Patent
Dyballa et al.

(10) Patent No.: US 10,227,278 B2
(45) Date of Patent: Mar. 12, 2019

(54) ECONOMICAL PRODUCTION OF 2-PROPYLHEPTANOL

(71) Applicant: Evonik Degussa GmbH, Essen (DE)

(72) Inventors: Katrin Marie Dyballa, Recklinghausen (DE); Robert Franke, Marl (DE); Dirk Fridag, Haltern am See (DE); Markus Schwarz, Haltern am See (DE); Hermann-Josef Schulte-Althoff, Haltern am See (DE); Frank Geilen, Haltern am See (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 15/773,613

(22) PCT Filed: Aug. 2, 2016

(86) PCT No.: PCT/EP2016/068375
§ 371 (c)(1),
(2) Date: May 4, 2018

(87) PCT Pub. No.: WO2017/080690
PCT Pub. Date: May 18, 2017

(65) Prior Publication Data
US 2018/0319727 A1 Nov. 8, 2018

(30) Foreign Application Priority Data

Nov. 9, 2015 (EP) ..................... 15193607

(51) Int. Cl.
| | | |
|---|---|---|
| C07C 45/50 | (2006.01) |
| C07C 47/02 | (2006.01) |
| C07C 29/17 | (2006.01) |
| C07C 29/14 | (2006.01) |
| C07C 47/21 | (2006.01) |
| B01J 31/02 | (2006.01) |
| B01J 31/18 | (2006.01) |

(52) U.S. Cl.
CPC ............ *C07C 29/177* (2013.01); *C07C 29/14* (2013.01); *C07C 45/50* (2013.01); *C07C 47/02* (2013.01); *C07C 47/21* (2013.01); *B01J 31/0237* (2013.01); *B01J 31/185* (2013.01); *B01J 2231/321* (2013.01); *B01J 2531/822* (2013.01)

(58) Field of Classification Search
CPC ......... C07C 45/50; C07C 47/02; C07C 29/14; C07C 47/21; B01J 2531/822; B01J 31/0237; B01J 31/185; B01J 2231/321
See application file for complete search history.

(56) References Cited

U.S. PATENT DOCUMENTS 8,461,394 B2 6/2013 Lueken et al.
2011/0130595 A1 6/2011 Lueken et al.

FOREIGN PATENT DOCUMENTS

DE 102008002187 A1 12/2009
WO WO 2005/009934 A2 2/2005

OTHER PUBLICATIONS

International Search Report dated Oct. 7, 2016, in PCT/EP2016/068375, filed Aug. 2, 2016.

*Primary Examiner* — Jafar F Parsa
(74) *Attorney, Agent, or Firm* — Oblon, McClelland, Maier & Neustadt, L.L.P.

(57) ABSTRACT

The production of 2-propylheptanol described here is effected via Rh-catalyzed hydroformylation of $C_4$-olefin to afford $C_5$-aldehyde, aldol condensation to afford the $C_{10}$-aldehyde and hydrogenation to afford the $C_{10}$-alcohol. The emphasis is on the hydroformylation and the ligand employed therein. The problem addressed by the invention is that of reducing the costs of 2PH production. This problem is solved when a cheaper catalyst system which simultaneously achieves a better regioselectivity is employed in the hydroformylation. This catalyst system contains rhodium as the central atom and is complexed with the ligand (1):

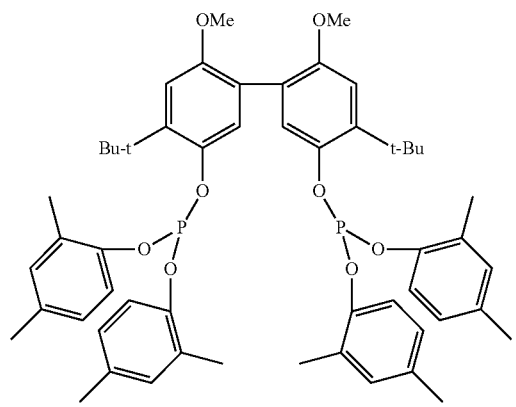

(1)

9 Claims, 4 Drawing Sheets

ECONOMICAL PRODUCTION OF 2-PROPYLHEPTANOL

The invention is concerned with the production of 2-propylheptanol.

2-propylheptanol (2PH) is a mixture of $C_{10}$-alcohols which is used as an intermediate for the production of plasticizers, detergents and lubricants.

The production of 2PH discussed here is effected via Rh-catalyzed hydroformylation of $C_4$-olefin to afford $C_5$-aldehyde, aldol condensation to afford the $C_{10}$-aldehyde and hydrogenation to afford the $C_{10}$-alcohol. The synthetic route per se is disclosed in EP2280920B1. The present application focuses on the hydroformylation and in particular on the ligands employed therein.

The ligand used in EP2280920B1 is depicted in formula (7).

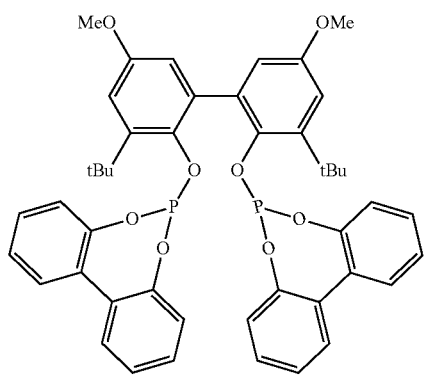

(7)

In the hydroformylation of an input mixture containing 35% 2-butene, only 1% 1-butene and the remainder inert butane this catalyst system achieved butene conversions of 65% to 75%. The percentage distribution between n-pentanal and 2-methylbutanal, the so-called n/iso selectivity, was at least 95% to 5%. The regioselectivity for n-pentanal was accordingly 95%.

The regioselectivity for a target product is an important measure of the efficiency of a reaction. Particularly when especially one of the two products is to be preferentially formed. In hydroformylation it indicates the n/iso selectivity of the ratio of the linear aldehyde (=n) to branched (=iso) aldehyde. N-pentanal regioselectivity indicates that this amount of linear product was formed. The remaining percentages then correspond to the branched isomer. A high regioselectivity for n-pentanal accordingly indicates that a comparatively large amount of the coveted product is formed.

In this respect it is hard to find fault with the ligand (7) used in EP2280920B1. However, one disadvantage of the catalyst system based on ligand (7) is that after an operating time of about 1000 h it causes a precipitate on the wall of the reactor. Analysis of the precipitate showed that it comprises phosphorus-containing descendant products of the bisphosphite ligand (7) and the employed amine. This means that despite the amine employed as a stabilizer the ligand described in EP2280920B1 breaks down after only a relatively short operating time for an industrially practicable process, thus reducing the conversion for the reaction.

Significant process improvements were achieved with the catalyst system described in EP2802550B1 which comprises at least one ligand of formulae (5) and (4):

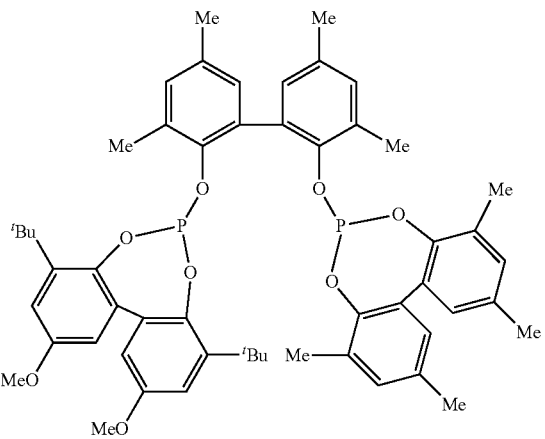

(5)

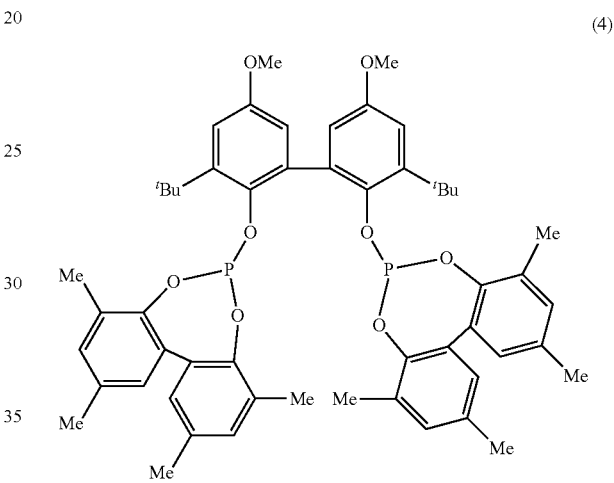

(4)

No accumulation of solid was determined over 8000 operating hours. Regioselectivity remained at a high level of approximately 93%; yield was between 60% and 80%.

Disadvantages of the catalyst system based on (4)/(5) compared to the catalyst system employing (7) as a ligand include not only poorer regioselectivity but also poorer efficiency of the synthesis for ligands (4) and (5): This is because both ligands exhibit a bridge between their adjacent phenol rings whose synthesis provides yields which are not nearly as good as for the biphenol building block of the ligand (7). Thus the catalyst system based on (4) and (5) is markedly more complex and inefficient in terms of production than the one utilizing the ligand (7). Nevertheless, a 2-PH process with the ligands (4) and (5) has the prolonged lifetime and the better process stability and the process described in EP2802550B1 is therefore ultimately better than that disclosed in EP2280920B1.

Yet there continues to be a need for improvement in making the process for 2PH production markedly more efficient. This is the problem addressed by the present invention.

This problem is solved when a catalyst system which may be produced by fewer synthesis steps and simultaneously achieves a better regioselectivity is employed in the hydroformylation. This catalyst system contains rhodium as the central atom and is complexed with the ligand (1):

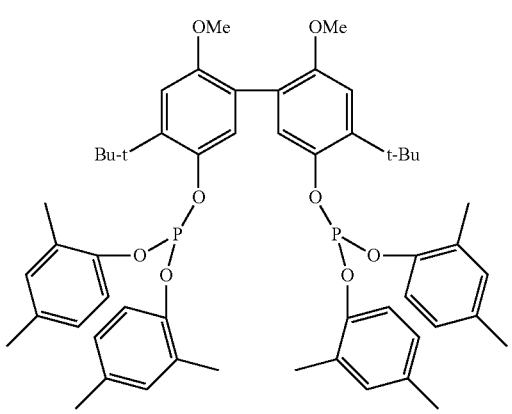

(1)

The IUPAC designation for ligand (1) is 3,3'-di-tert-butyl-5,5'-dimethoxy-[1,1'-biphenyl]-2,2'-diyltetrakis(2,4-dimethylphenyl)bis(phosphite).

The advantage of the ligand (1) compared to (7) is its better long-term stability. Compared to (5) and (4), (1) is markedly more efficient in terms of production/synthesis of the ligand since the ligand employed according to the invention requires one less synthesis step. The ligand synthesis then proceeds more rapidly and therefore entails less reactor downtime for ligand production and fewer waste products are generated too. This is an important argument in particular against the backdrop of sustainability which is increasingly demanded of the chemical industry. Furthermore the regioselectivity of (1) is markedly better than that of (5) and (4) and a process catalyzed therewith accordingly forms markedly more coveted n-pentanal than less desired isopentanal. The regioselectivity of (1) compared to (7) is slightly better.

Figure 1:
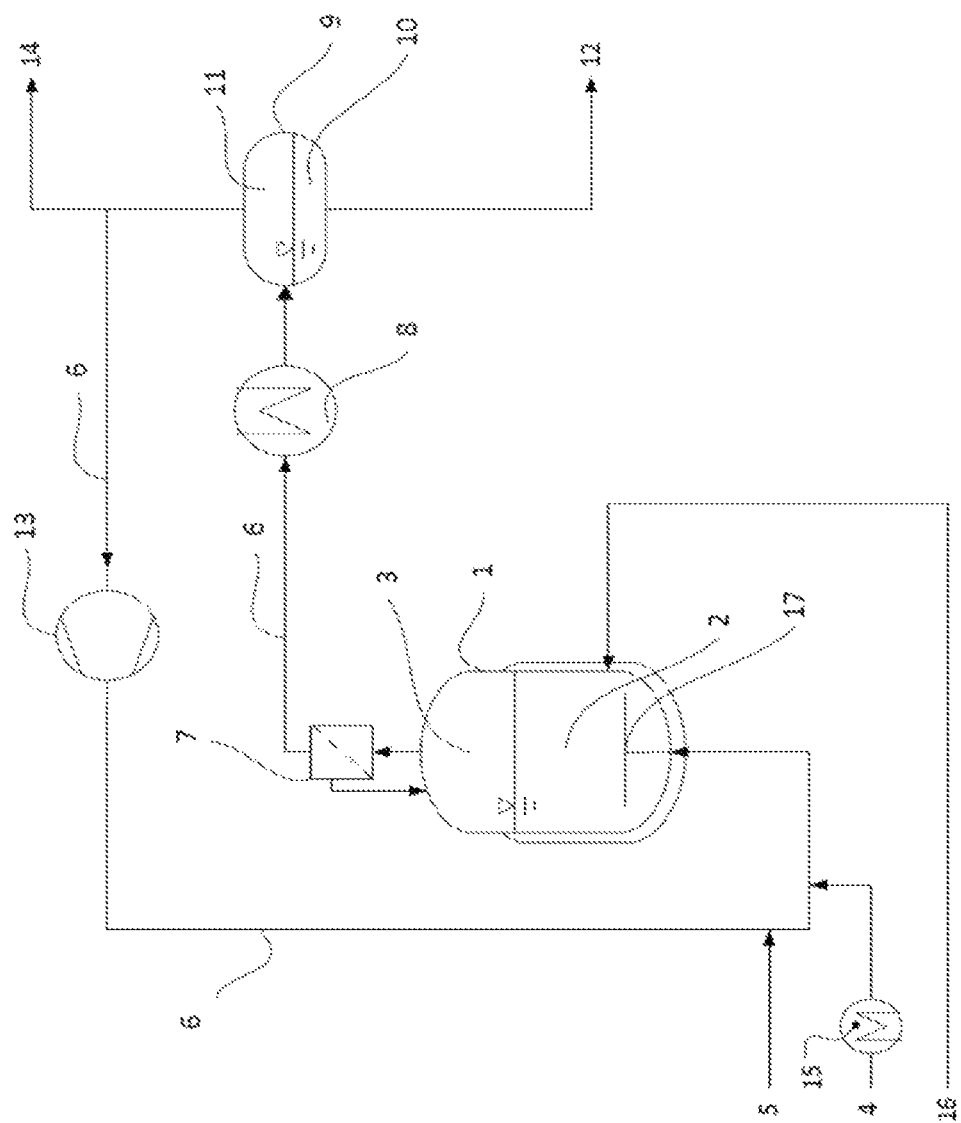
FIG. 1 is a schematic diagram of pilot plant used.

The invention accordingly provides a process for producing 2-propyl-1-heptanol comprising the steps of:
a) providing an input mixture containing at least cis-2-butene and/or trans-2-butene;
b) treating the input mixture with carbon monoxide and hydrogen in the presence of a homogeneous catalyst system comprising rhodium and at least one organophosphorus compound as a ligand at a temperature between 110° C. and 150° C. and a pressure between $10*10^5$ Pa and $30*10^5$ Pa to perform a hydroformylation to obtain a first reaction mixture containing at least n-pentanal and isopentanal;
c) obtaining an aldehyde fraction containing n-pentanal and isopentanal from the first reaction mixture;
d) subjecting the aldehyde fraction to an aldol condensation in the presence of an aqueous base to obtain a second reaction mixture comprising an aqueous phase and an organic phase, wherein the organic phase contains at least 2-propylhept-2-enal;
e) separating the organic phase from the aqueous phase;
f) treating the organic phase with hydrogen in the presence of a heterogeneous catalyst to perform a hydrogenation to obtain a third reaction mixture containing at least 2-propyl-1-heptanol;
g) obtaining a target fraction containing 2-propyl-1-heptanol from the third reaction mixture;
wherein the improvement consists in
the homogeneous catalyst system comprising at least the organophosphorus compound according to formula (1) as a ligand:

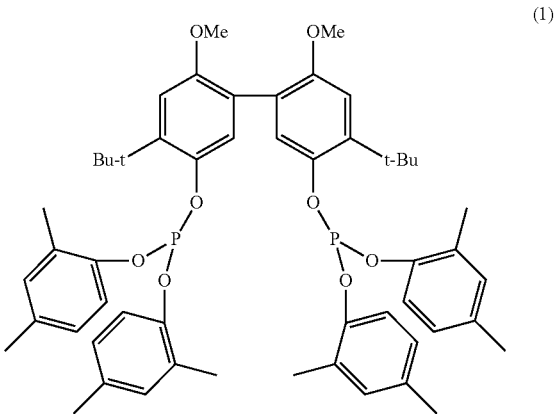

(1)

One peculiarity of the ligand (1) described here is that it is employed at comparatively high temperatures of around 130° C. The reason for this is that the yield of this ligand is better at 130° C. than at 120° C. By contrast, according to the examples of EP2280920B1 and EP2802550B1 the ligands (7) and (4)/(5) are employed at only 120° C. Accordingly a preferred development of the invention provides that step b) of the process is performed at a temperature between 120° C. and 140° C. The pressure is preferably between $15*10^5$ Pa and $25*10^5$ Pa.

Using the ligand (1) at temperatures around 130° C. allows a substrate formed from cis-2-butene and trans-2-butene to be converted to an extent of 50% to 70% in the hydroformylation (yield in the direction of the $C_5$-aldehydes). N-pentanal then accounts for 96% to 99% thereof. The regioselectivity for n-pentanal thus achieves a value between 96% and 99%. Provided the input mixture also contains 1-butene this likewise forms part of the substrate in the context of the present application and is included in the calculation of regioselectivity.

Other than isolated metrology-dependent outliers this high regioselectivity can be maintained over a period of at least 2000 h.

To increase operating duration the hydroformylation is performed in the presence of an organic amine of formula (3) is

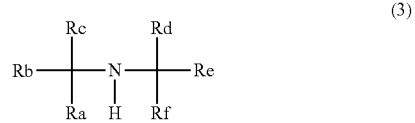

(3)

in which Ra, Rb, Rc, Rd, Re and Rf represent identical or different hydrocarbon radicals which may also be joined to one another. The organic amine preferably comprises at least one 2,2,6,6-tetramethylpiperidine unit. Specifically the organic amine may be a di-4-(2,2,6,6-tetramethylpiperidinyl) sebacate.

An input for the hydroformylation that has proven advantageous is a mixture having the following composition summing to 100% by weight:

Sum of cis-2-butene and trans-2-butene: 10% by weight to 50% by weight;
1-Butene: 0% to 5% by weight;
Sum of n-butane and isobutane: 50% by weight to 90% by weight;
Sum of other substances: 0% to 1% by weight.

The hydroformylatable substrate is accordingly formed substantially by the cis-2-butene and the trans-2-butene. Provided that the mixture also contains 1-butene this is likewise to be regarded as part of the substrate since it likewise forms n-pentanal in the hydroformylation. Such an input mixture is comparatively cheap since it contains hardly any 1-butene and lots of inert butane. Since the catalyst system described here has such a good regioselectivity and is able to effect isomerizing hydroformylation of the recited substrates having an internal double bond with high n-selectivity, lots of n-pentanal may be formed despite the high fraction of 2-butene. This ultimately renders the overall process particularly efficient.

It is recommended to establish a rhodium concentration in the first reaction mixture between 1 ppmw and 1000 ppmw. The ligand/rhodium ratio should be between 1:1, to 100:1 and no further ligand is to be provided as part of the homogeneous catalyst system in addition to the organophosphorus compound according to formula (1). In industrial operation it cannot be ruled out that owing to impurities organophosphorus compounds other than 3,3'-di-tert-butyl-5,5'-dimethoxy-[1,1'-biphenyl]-2,2'-diyltetrakis(2,4-dimethylphenyl)bis(phosphite) complex to the rhodium as part of the catalyst system. However, such impurities can be disregarded at the indicated ligand/rhodium ratio. This relates solely to ligand (1) and no further ligand need be intentionally provided.

Other than the particular mandates described here the hydroformylation is operated as is customary in the prior art.

The remaining synthesis steps are likewise effected in a conventional manner. Reference is made to the following documents for example: Hydroformylation: EP2280920B1 (workup of the aldehydes), EP2802550B1 (cycle gas process, with further references); aldol condensation: DE19957522A1 (reaction conditions), DE102009045139A1 (reaction engineering), DE102009001594A1 (phase separation). The hydrogenation is likewise effected according to the processes known per se, for example in the temperature range from 170° C. to 200° C. at a pressure of $15*10^5$ Pa to $30*10^5$ Pa over a supported catalyst which contains as active components at least nickel and copper; cf. EP3037400A1.

The invention will now be elucidated in detail with reference to examples.

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}P$ NMR signals were referenced as follows: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

The synthesis of comparative ligands (4) and (5) is effected according to the reaction equation:

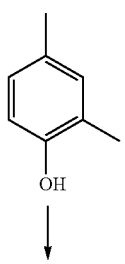

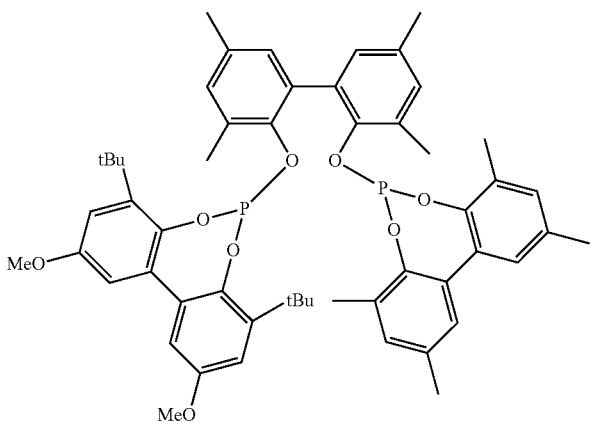

(5)

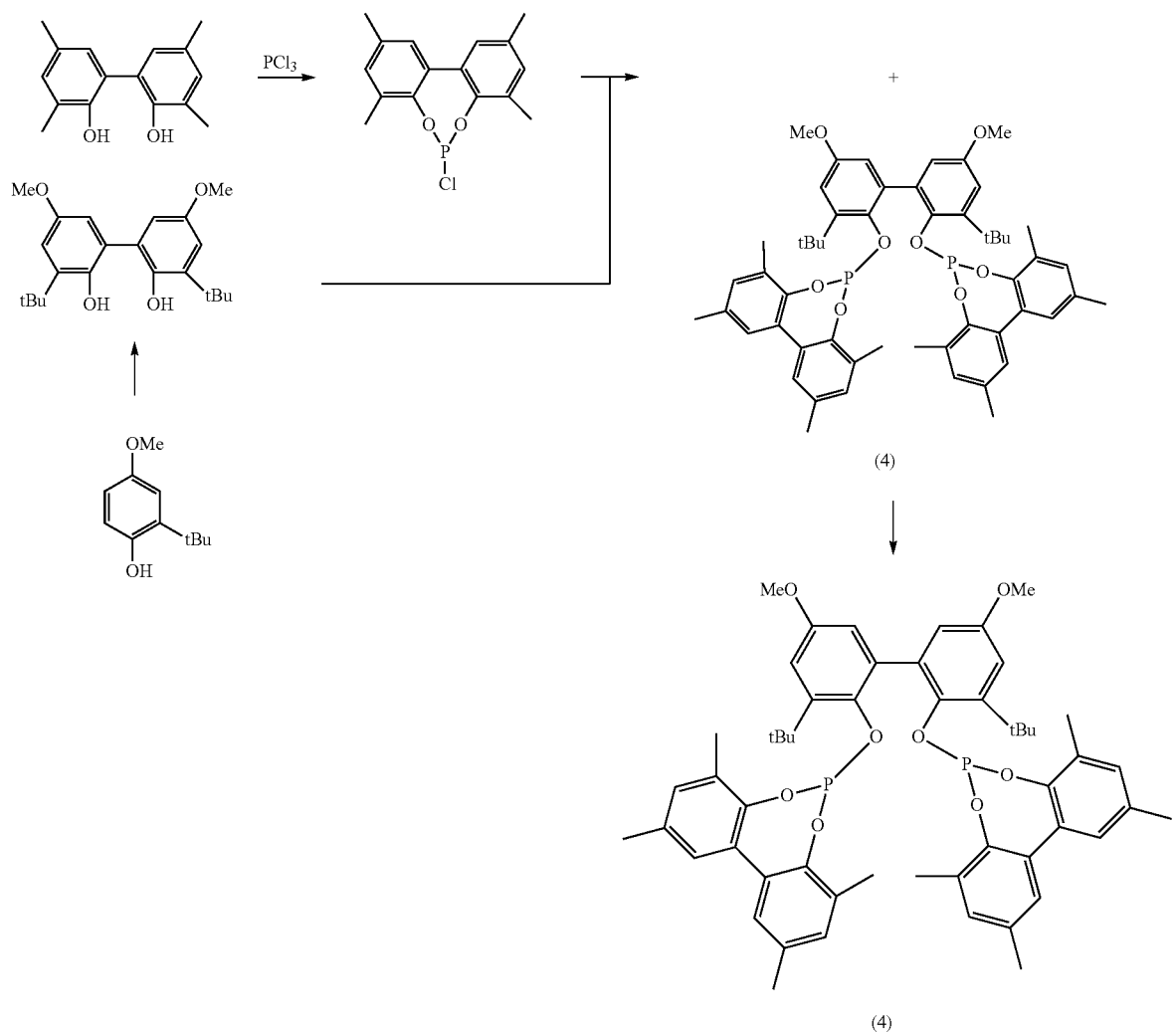
(4)
A detailed description of the synthesis may be found in WO 2014/056735A1.
The synthesis of the inventive ligand (1) is effected according to the reaction equation:
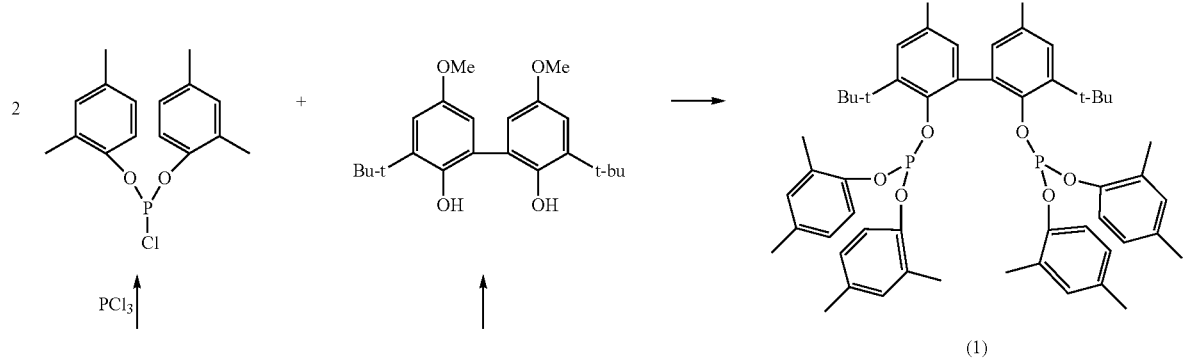

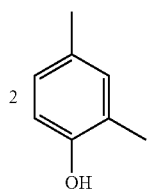 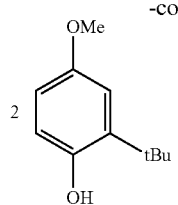

As is apparent from a comparison of the two reaction schemes fewer synthesis steps are required for the inventive compound (1) than for the compounds (4) or (5) used in EP2802550B1. In the production of compound (1) the 2,4-dimethylphenol need not first be coupled to a biphenol but rather may be converted to the corresponding chlorophosphite directly with PCl₃.

Production of bis(2,4-dimethylphenyl)chlorophosphite

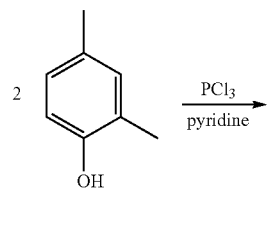

50 g of PCl₃ (0.363 mol) and 86 g of pyridine (1.076 mol) in 380 ml of dried toluene were initially charged in a secured 1200 ml glass reactor provided with a dropping funnel. The milky yellow PCl₃/pyridine solution was cooled down to −7° C. with stirring. 86 ml of 2,4-dimethylphenol (0.720 mol) were then added to the dropping funnel and dissolved in 380 ml of dried toluene. To carry out the reaction, the phenol/toluene solution was added dropwise slowly and steadily to the PCl₃/pyridine solution. The reaction mixture was brought to room temperature overnight with stirring.

For workup, the hydrochloride formed was filtered off and rinsed with 60 ml of dried toluene and the resulting mother liquor was concentrated to dryness under reduced pressure. The solvent is removed completely until a solid is formed.

For further workup, the crude solution was distilled. To this end the crude solution was filled into a pear-shaped flask onto which a short distillation apparatus without a cooling jacket was placed. The thermometer was placed at the upper opening, and at the other end a spider with four further pear-shaped flasks was attached. Subsequently, this apparatus was attached to a cold trap and from there to the high vacuum pump. The pear-shaped flask with the crude ligand to be distilled was heated by means of an oil bath. Firstly, the forerun was removed at a head temperature of 25-30° C. The spider was then further rotated and the main run was removed at a head temperature of 140° C. When no more drops appeared in the main run, the distillation was stopped, the pump was shut down and the main run in the relevant pear-shaped flask was removed, sealed and analysed. A total mass of 56.7 g was ultimately obtained. This corresponds to a yield of 46%.

Production of 3,3'-di-tert-butyl-5,5'-dimethoxy-[1,1'-biphenyl]-2,2'-diyltetrakis(2,4-dimethylphenyl)bis(phosphite):

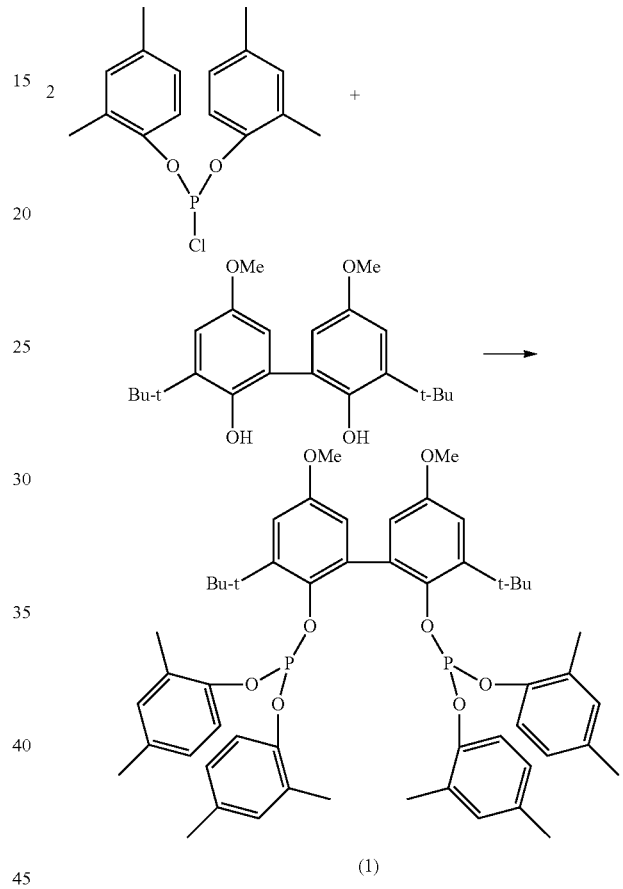

In a 1000 ml Schlenk flask, 260 ml of dried acetonitrile were added to 51.86 g (0.153 mol) of bis(2,4-dimethylphenyl)chlorophosphite at room temperature with stirring and the chlorophosphite was dissolved.

In a second 250 ml Schlenk flask, 12.4 ml (0.153 mol) of pyridine and 155 ml of dried acetonitrile were added to 20.1 g (0.056 mol) of 3,3'-di-tert-butyl-5,5'-dimethoxy-[1,1'-biphenyl]-2,2'-diol. The chlorophosphite solution in the Schlenk flask was then cooled to 0° C. The biphenol/pyridine solution was then added dropwise slowly with vigorous stirring. The reaction mixture was maintained at this temperature for about 3 h and then very slowly brought to room temperature overnight. The suspension was then filtered off, washed thoroughly with 30 ml of acetonitrile and dried. A mass of 44.01 g was ultimately obtained. This corresponds to a yield of 85%.

In order to reduce the chlorine content in this crude ligand, said ligand was purified. The reported chlorine contents are to be understood as meaning total chlorine contents. The total chlorine content is determined according to Wickbold: sample preparation according to DIN 51408 and analysis by ion chromatography according to DIN EN ISO 10304.

5.15 g of 3,3'-di-tert-butyl-5,5'-dimethoxy-[1,1'-biphenyl]-2,2'-diyltetrakis(2,4-dimethylphenyl)bis(phosphite) were stirred in a 250 ml Schlenk flask with 15 ml of degassed toluene and 5 ml of pyridine at 100° C. After all had dissolved, the temperature was maintained for a further 15 min followed by cooling to 90° C.

Meanwhile, 100 ml of heptane and 5 ml of pyridine were placed in another 250 ml Schlenk flask and the solution was cooled down to 0° C. Subsequently, the solution with the 3,3'-di-tert-butyl-5,5'-dimethoxy-[1,1'-biphenyl]-2,2'-diyltetrakis(2,4-dimethylphenyl)bis(phosphite) was added via the frit to the cold heptane/pyridine solution and stirred at 0° C. for 3 h. Here too, nothing precipitated out. Thus here too the solvent was withdrawn by means of a vacuum pump off until the solid had precipitated and dried. A mass of 3.7 g was ultimately obtained. The chlorine determination gave a value of 20/20 ppm.

Catalysis experiments were then performed with the thus produced ligands. The general procedure for this was as follows:

In a 100 ml autoclave from Parr Instruments, synthesis gas (mixture of hydrogen and carbon monoxide; volumetric CO:H2 ratio=1:1) was used to hydroformylate pure cis-2-butene. Rh(acac)(CO)$_2$ in toluene was initially charged as precursor. The ligand was used in molar excesses of 4:1 relative to rhodium. A di-4-(2,2,6,6-tetramethylpiperidinyl) sebacate (Tinuvin 770DF from BASF) was used as stabilizer in a molar ratio to the ligand of about 1:1. In addition, about 0.5 g of tetraisopropylbenzene (TIPB) was added as GC standard. About 6 g of reactant were metered in after the intended reaction temperature had been attained.

During the reaction, the pressure was kept constant via a synthesis gas control means having a mass flow meter. The stirrer speed was 1200 min$^{-1}$. Samples were taken from the reaction mixture after 12 hours. The results of the experiments are summarized in Table 1.

Hydroformylation with inventive ligand (1):

In a 100 mL autoclave from Parr Instruments 5.6 g of cis-2-butene were hydroformylated at 120° C. and 20*10$^5$ Pa of synthesis gas pressure. 0.0056 g of Rh(acac)(CO)$_2$ in 48.8 g of toluene was initially charged as precursor. 0.0779 g of ligand was employed in the catalyst batch solution as the ligand. 0.0416 g of di-4-(2,2,6,6-tetramethylpiperidinyl) sebacate (Tinuvin 770DF from BASF) as organic amine and 0.5760 g of tetraisopropylbenzene as GC standard were added. The reactant was metered in after the intended reaction temperature had been attained. During the reaction, the pressure was kept constant via a synthesis gas control means having a mass flow meter. Samples were taken from the reaction mixture after 12 hours.

Hydroformylation with noninventive ligands (4) and (5):

For comparison, compound (5) and its symmetric isomer compound (4) were tested under identical conditions. The hydroformylation results of pure cis-2-butene at 20*10$^5$ Pa of synthesis gas pressure and at a temperature of 120° C. are reported in Table 1.

TABLE 1

Results of experiments in autoclave

| Ligand | Aldehyde yield in [%] | n-Pentanal regioselectivity in [%] |
|---|---|---|
| (5) | 95 | 94 |
| (4) | 66 | 90 |
| (1) | 95 | 98 |

Discussion of results:

The noninventive ligand (5) shows a very good n-pentanal regioselectivity of 94% and good aldehyde yields. Its symmetric isomer (4) shows a lower regioselectivity for n-pentanal of only 90% and markedly lower yields. The best regioselectivity of 98% is achieved by the inventive ligand (1). This is in fact even higher than the 95% achieved by the noninventive ligand (7) in EP2280920B1.

Ligand (1) was convincing in the long term experiment too:

EXAMPLE 1: HYDROFORMYLATION WITH THE NONINVENTIVE LIGAND (7)

The noninventive ligand of formula (7) known from EP2280920B1 was used in the hydroformylation of a butene/butane mixture. Ligand (7) was stabilized with di-4-(2,2,6,6-tetramethylpiperidinyl) sebacate.

The continuously operated pilot plant consisted essentially of a pressure reactor of capacity 20 liters with a downstream condenser and phase separation vessel (gas/liquid) for the gas phase originating from the reactor, and a cycle gas compressor which returns the gas phase from the phase separation vessel back down into the reaction zone. A portion of this cycle gas is run out of the reaction system as offgas after the phase separation. In order to achieve optimal gas distribution in the reactor system, a gas distributor ring with bores was installed here. The reactor was temperature controllable via installed heating and cooling apparatuses. The pilot plant is shown in schematic form in FIG. 1.

FIG. 1: Schematic diagram of pilot plant used.

Prior to the hydroformylation, the system was purged with nitrogen to free it of oxygen. The reactor was subsequently filled with catalyst solution. This catalyst solution was composed of 12 kg of Vestinol® INB (CAS 670241-72-2), 4.5 g of Rh(acac)(CO)$_2$, 54.9 g of bisphosphite ligand of formula (7) and 50.4 g of di-4-(2,2,6,6-tetramethylpiperidinyl) sebacate (Tinuvin 770DF from BASF) and was previously mixed in a container. The Vestinol® INB was previously stripped with nitrogen to remove oxygen and water therefrom.

Subsequently, the reactor system was purged with synthesis gas to free it of nitrogen. Once the nitrogen content had fallen below 10% by volume, the reactor system was pressurized to 1.0 MPa with synthesis gas and then heated to 130° C. On attainment of the operating temperature, the reactor system was brought to a reaction pressure of 1.7 MPa with synthesis gas.

Then the addition of the starting materials was commenced. To this end, an input mixture was run through an evaporator in order to introduce it into the cycle gas in gaseous form. The input mixture was a mixture of 35% by weight of 2-butene and 1-butene in a concentration of about 1% by weight. The remainder was n-butane. The following throughputs were established: 0.5 kg/h of input mixture, 350 l (STP)/h of synthesis gas (50% by volume of H$_2$ and 50% by volume of CO).

For subsequent metered addition of the bisphosphite ligand (7) a 0.75% solution of the bisphosphite ligand (7) in n-pentanal previously freed of residual $C_4$-hydrocarbons (<3%) by stripping with nitrogen was made up. The Tinuvin 770DF was used in a twofold molar excess relative to the bisphosphite ligand (7). For better stabilization of this solution, the Tinuvin 770DF was added to the solution before the bisphosphite ligand (7).

The reaction products were continuously removed from the reactor via the cycle gas stream and partially condensed out in a condenser at 40° C. The condensed phase was continuously run out of the phase separation vessel. To determine conversion, samples were taken from the cycle gas upstream and downstream of the reactor and analysed by gas chromatography. Under the reaction conditions chosen, aldehyde yields of around 75% to 90% were achieved.

To determine the concentration of the free ligand not bonded to the rhodium, samples were taken from the reactor and analyzed by liquid chromatography (HLPC). By metered addition of the above-described ligand solution the concentration of the ligand in the reaction solution in the reactor was kept constant at a one-fold molar excess of the non-bonded ligand based on the employed rhodium.

The percentage distribution between n-pentanal and 2-methylbutanal, i.e. the regioselectivity, was 96% to 4%. The yield of the $C_5$-aldehydes and the regioselectivity over the experiment time are plotted in FIG. 2.

Figure 2:
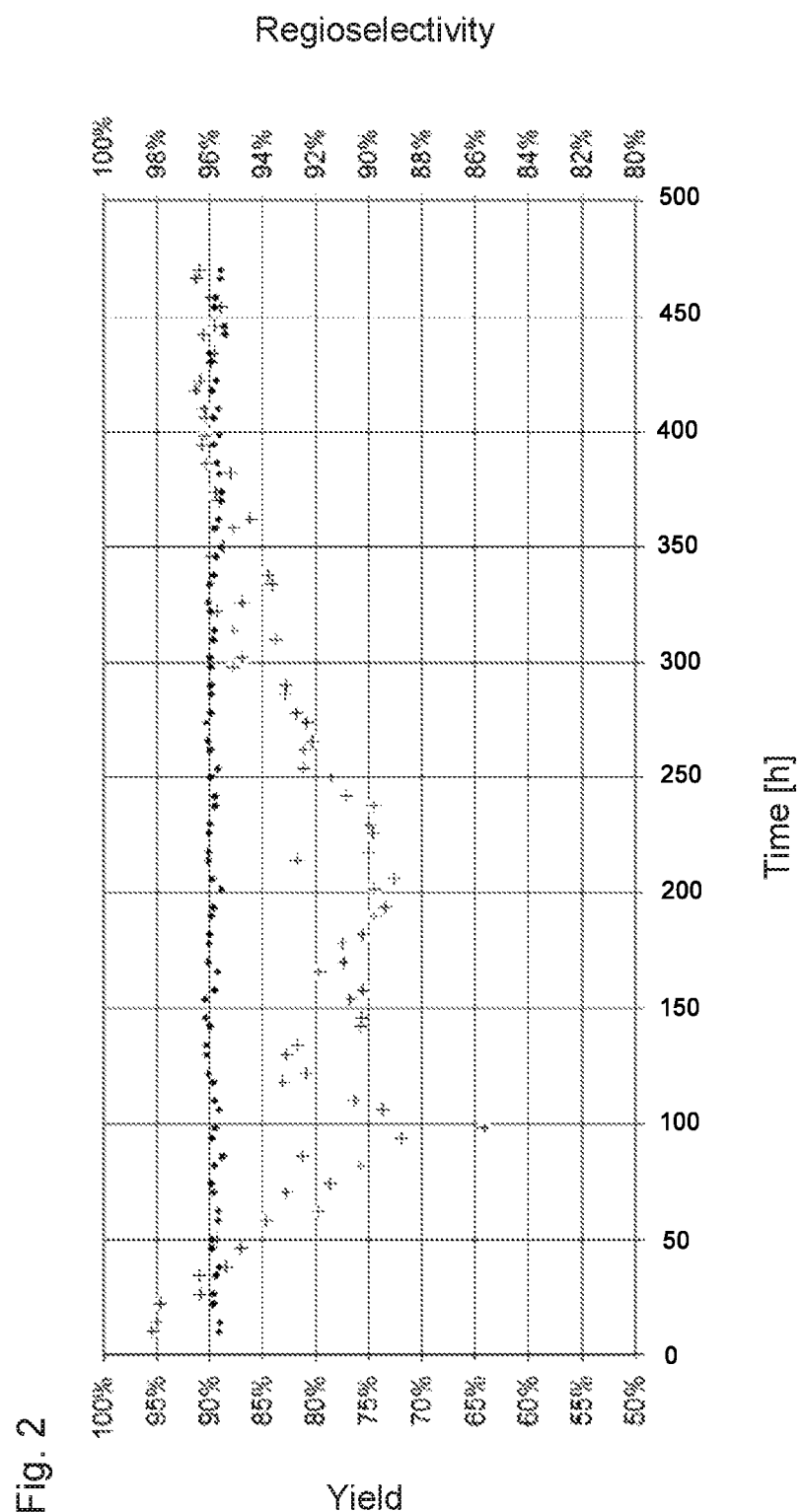
FIG. 2 is a diagram of $C_5$ yield (plus +) and regioselectivity for n-pentanal (point •) over time for Example 1.

FIG. 2: Diagram of $C_5$ yield (plus +) and regioselectivity for n-pentanal (point •) over time for Example 1

EXAMPLE 2: HYDROFORMYLATION WITH THE INVENTIVE LIGAND (1)

The same pilot plant as in Example 1 was used; cf. FIG. 1. The same input mixture and the same synthesis gas were used. However, the organophosphorus compound according to formula (1) was employed as ligand. The ligand of formula (7) known from EP2280920B1 was not present in the reaction mixture. The same Tinuvin 770DF as in Comparative Example 1 was used as stabilizer.

Prior to the hydroformylation, the system was purged with nitrogen to free it of oxygen. The reactor was subsequently filled with catalyst solution. This catalyst solution was composed of 12 kg of Vestinol® INB (CAS 670241-72-2), 4.5 g of Rh(acac)(CO)$_2$, 46.2 g of bisphosphite ligand of formula (1), 49.2 g of Tinuvin 770DF and was previously mixed in a container. The Vestinol® INB was previously stripped with nitrogen to remove oxygen and water therefrom.

Subsequently, the reactor system was purged with synthesis gas to free it of nitrogen. Once the nitrogen content had fallen below 10% by volume, the reactor system was pressurized to 1.0 MPa with synthesis gas and then heated to 120° C. On attainment of the operating temperature, the reactor system was brought to reaction pressure 1.7 MPa with synthesis gas.

Then the addition of the starting materials was commenced. To this end, an input mixture was run through an evaporator in order to introduce it into the cycle gas in gaseous form. The input mixture was again the mixture of 35% by weight of 2-butene and 1-butene in a concentration of about 1% by weight. The remainder was n-butane. The following throughputs were established: 0.5 kg/h of input mixture, 270 l (STP)/h of synthesis gas (50% by volume of $H_2$ and 50% by volume of CO).

For subsequent metered addition of the bisphosphite ligand (1) a 0.75% solution of the bisphosphite ligand (1) in n-pentanal previously freed of residual $C_4$-hydrocarbons (<3%) by stripping with nitrogen was made up. The Tinuvin 770DF was used in a twofold molar excess relative to the bisphosphite ligand (1). For better stabilization of this solution, the Tinuvin 770DF was added to the solution before the bisphosphite ligand (1).

The reaction products were continuously removed from the reactor via the cycle gas stream and partially condensed out in a condenser at 40° C. The condensed phase was continuously run out of the phase separation vessel. To determine conversion, samples were taken from the cycle gas upstream and downstream of the reactor and analysed by gas chromatography.

Under the reaction conditions chosen, aldehyde yields of around 40% to 50% were achieved.

To determine the concentration of the ligand not bonded to the rhodium, samples were taken from the reactor and analyzed by liquid chromatography (HLPC). By metered addition of the above-described ligand solution the concentration of the ligand in the reaction solution in the reactor was kept constant at a one-fold molar excess of the non-bonded free ligand based on the employed rhodium.

After 350 h the reaction temperature was increased from 120° C. 130° C. This resulted in a yield enhancement and the yield achieved values between 50% and 70%. The percentage distribution between n-pentanal and 2-methylbutanal, i.e. the regioselectivity, was at least 97% n-pentanal to 3% 2-methylbutanal. The yield of the $C_5$-aldehydes and the regioselectivity over the experiment time are plotted in FIG. 3.

Figure 3:
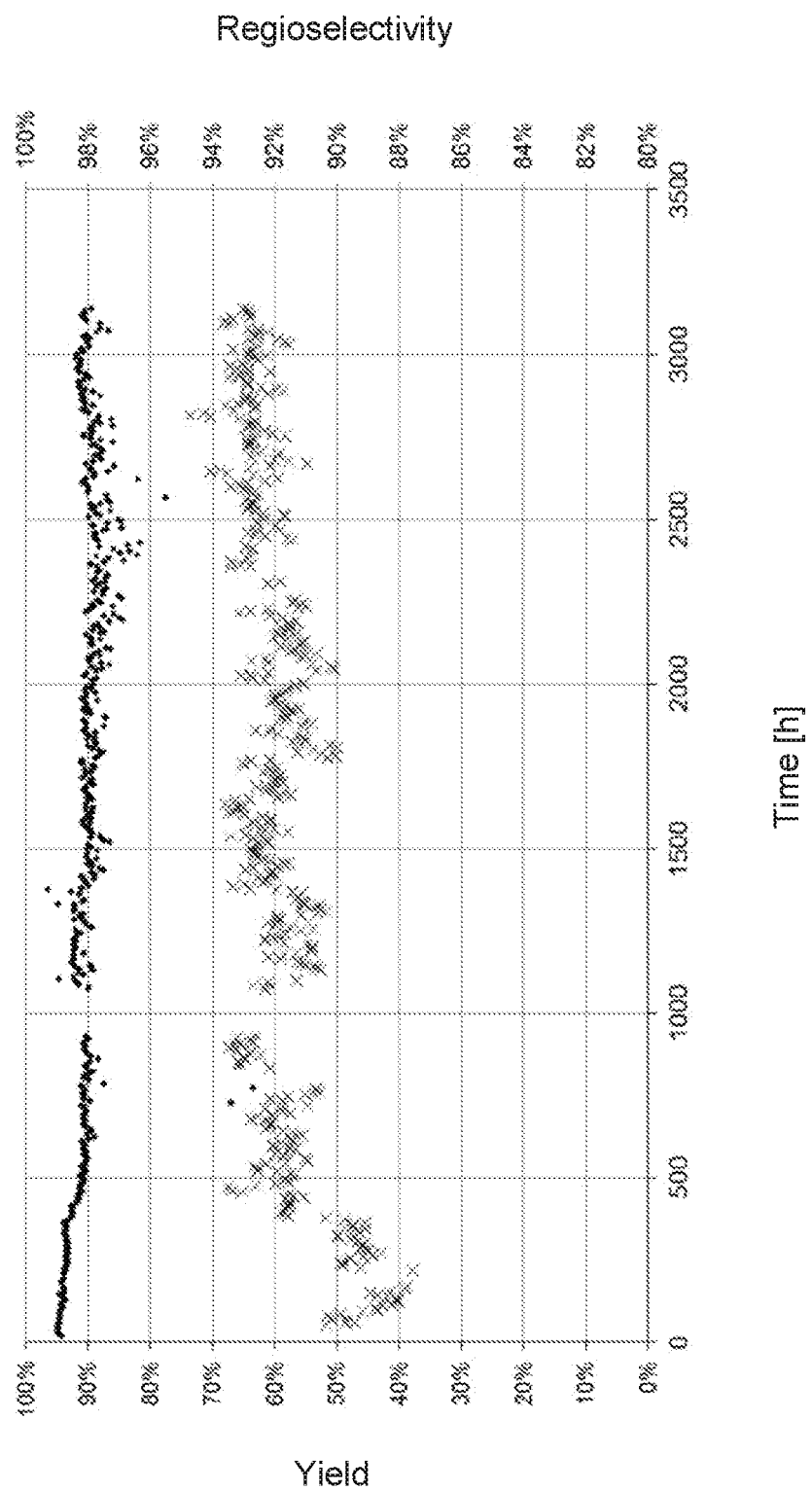
FIG. 3 is a diagram of $C_5$ yield (cross x) and regioselectivity for n-pentanal (diamond ♦) over time for Example 2.

FIG. 3: Diagram of $C_5$ yield (cross x) and regioselectivity for n-pentanal (diamond ♦) over time for Example 2

No deposits were observed in the pilot plant over the experiment duration.

EXAMPLE 3: HYDROFORMYLATION WITH THE NONINVENTIVE LIGAND (5)

The noninventive ligand of formula (5) known from EP2802550B1 was used in the hydroformylation of a butene/butane mixture. Ligand (5) was stabilized with di-4-(2,2,6,6-tetramethylpiperidinyl) sebacate.

The pilot plant shown in FIG. 1 and also used in Examples 1 and 2 was employed once again.

Prior to the hydroformylation, the system was purged with nitrogen to free it of oxygen. The reactor was subsequently filled with catalyst solution.

This catalyst solution was composed of 12 kg of Vestinol® INB (CAS 670241-72-2), 4.5 g of Rh(acac)(CO)$_2$, 47.1 g of bisphosphite ligand of formula (5), 50.4 g of Tinuvin 770DF and was previously mixed in a container. The Vestinol® INB was previously stripped with nitrogen to remove oxygen and water therefrom.

Subsequently, the reactor system was purged with synthesis gas to free it of nitrogen. Once the nitrogen content had fallen below 10% by volume, the reactor system was pressurized to 1.0 MPa with synthesis gas and then heated to 130° C. On attainment of the operating temperature, the reactor system was brought to reaction pressure 1.7 MPa with synthesis gas.

Then the addition of the starting materials was commenced. For this purpose, an input mixture was run through an evaporator in order to run it into the cycle gas in gaseous form. The input mixture was again the mixture of 35% by weight of 2-butene and 1-butene in a concentration of about 1% by weight. The rest was n-butane. The following throughputs were set: 0.5 kg/h of input mixture, 250 l (STP)/h of synthesis gas (50% by vol. of $H_2$ and 50% by vol. of CO).

For subsequent metered addition of the bisphosphite ligand (5) a 0.75% solution of the bisphosphite ligand (5) in n-pentanal previously freed of residual $C_4$-hydrocarbons (<3%) by stripping with nitrogen was made up. The Tinuvin 770DF was used in a twofold molar excess relative to the bisphosphite ligand (5). For better stabilization of this solution, the Tinuvin 770DF was added to the solution before the bisphosphite ligand (5).

The reaction products were removed continuously from the reactor via the cycle gas stream and partially condensed out in a condenser at 40° C. The condensed phase was run continuously out of the phase separation vessel. To determine conversion, samples were taken from the cycle gas upstream and downstream of the reactor and analysed by gas chromatography. Under the reaction conditions chosen, aldehyde yields of around 80% to 85% were achieved.

To determine the concentration of the free ligand not bonded to the rhodium, samples were taken from the reactor and analyzed by liquid chromatography (HLPC). By metered addition of the above-described ligand solution the concentration of the ligand in the reaction solution in the reactor was kept constant at a one-fold molar excess of the non-bonded ligand based on the employed rhodium.

The percentage distribution between n-pentanal and 2-methylbutanal, i.e. the regioselectivity, was 93% to 7%. The yield of the $C_5$-aldehydes and the regioselectivity for n-pentanal over the experiment time are plotted in FIG. 4.

Figure 4:
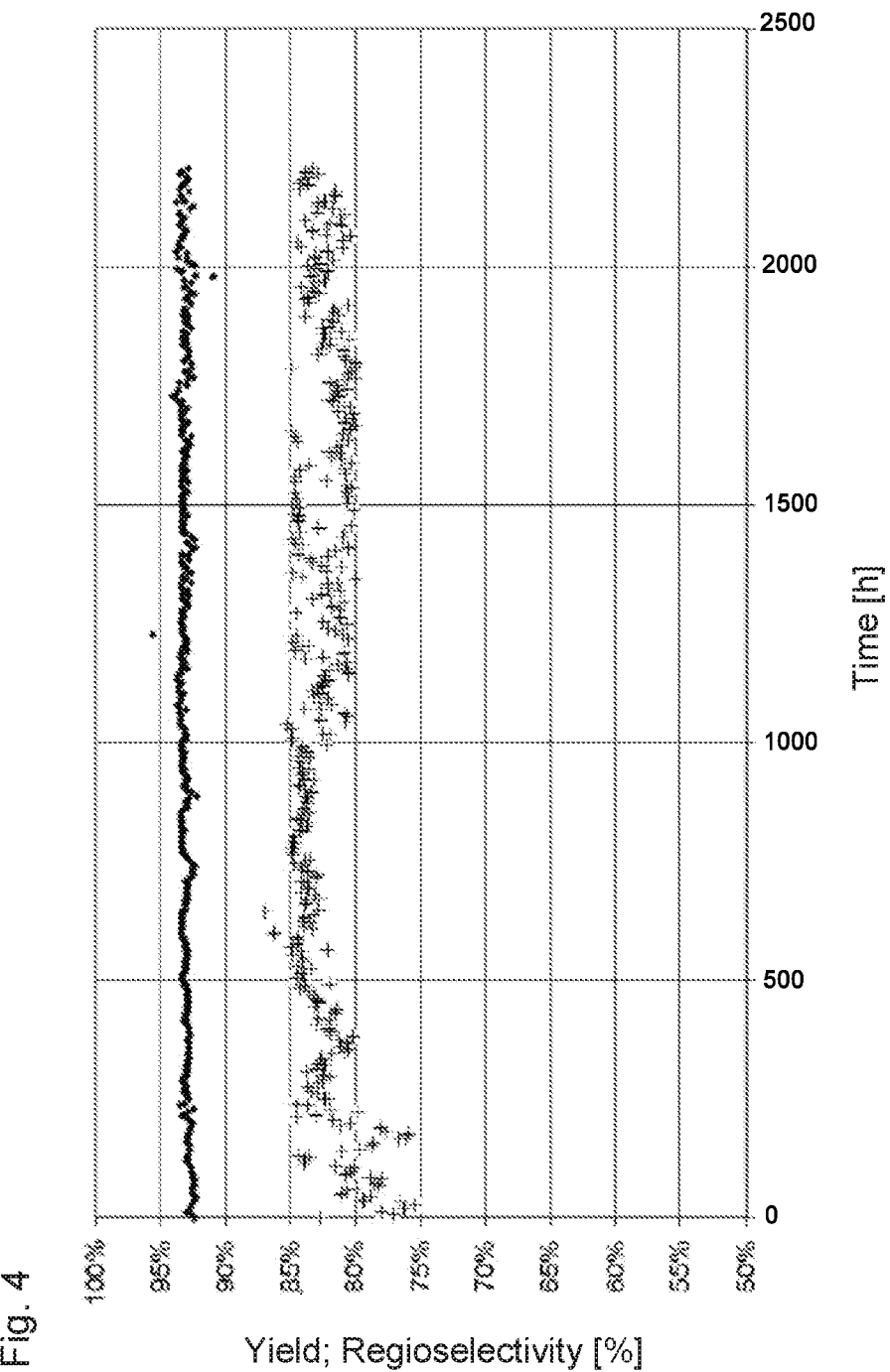
FIG. 4 is a diagram of $C_5$ yield (plus x) and regioselectivity for n-pentanal (diamond ♦) over time for Example 3.

FIG. 4: Diagram of $C_5$ yield (plus x) and regioselectivity for n-pentanal (diamond ♦) over time for Example 3

CONCLUSION

The results of the long-term experiments afforded in Examples 1, 2 and 3 are summarized in Table 2

TABLE 2

Results of the long-term experiments

| Example No. | Ligand formula | According to the invention | Temperature | $C_5$ yield | Regioselectivity for n-pentanal |
|---|---|---|---|---|---|
| 1 | (7) | no | 130° C. | 75% to 90% | 96% |
| 2; t < 350 h | (1) | yes | 120° C. | 40% to 50% | >98% |
| 2; t > 350 h | (1) | yes | 130° C. | 50% to 70% | >97% |
| 3 | (5) | no | 130° C. | 80% to 85% | 93% |

The long-term experiments performed confirm the early laboratory finding that the organophosphorus compound (1) employed according to the invention achieves a higher regioselectivity for n-pentanal than the ligands (7) and (5) of the prior art. Better $C_5$ yields can be expected at 130° C. than at 120° C., though they remain behind those of the prior art. However, this disadvantage is compensated by the better long-term stability than ligand (7) and the lower synthesis costs than ligand (5).

Since the higher regioselectivity results in an increased production of the intermediate n-pentanal, which in turn is converted more rapidly into $C_{10}$-aldehyde in the subsequent aldol condensation, the overall process, production of 2-propylheptanol from 2-butene, is chemically markedly more efficient than the processes of the prior art. Compared to the process with ligand (7) described in EP2280920B1 production costs can be reduced since the ligand (1) employed according to the invention exhibits longer service lifetimes. Compared to the process described in EP2802550B1 the process according to the invention is more cost-effective since the ligand (7) requires fewer synthesis steps than the ligands (4) and (5) and may therefore be produced more efficiently. These synergistic effects ultimately allow a markedly more economic production of 2-propylheptanol.

LIST OF REFERENCE NUMERALS FOR FIG. 1

1 reactor
2 liquid phase
3 gaseous phase
4 input mixture
5 synthesis gas
6 cycle gas
7 aerosol breaker
8 condenser
9 phase separation vessel
10 condensate
11 uncondensed fractions of the cycle gas
12 workup
13 cycle gas compressor
14 offgas
15 evaporator
16 ligand solution
17 gas distributor

The invention claimed is:

1. A process for producing 2-propyl-1-heptanol, the process comprising:

treating an input mixture containing at least cis-2-butene and/or trans-2-butene with carbon monoxide and hydrogen in the presence of a homogeneous catalyst system comprising rhodium and at least one organophosphorus compound of formula (1) as a ligand at a temperature between 110° C. and 150° C. and a pressure between $10*10^5$ Pa and $30*10^5$ Pa to perform a hydroformylation to obtain a first reaction mixture containing at least n-pentanal and isopentanal;

subjecting an aldehyde fraction containing n-pentanal and isopentanal from the first reaction mixture to an aldol condensation in the presence of an aqueous base to obtain a second reaction mixture comprising an aqueous phase and an organic phase, wherein the organic phase contains at least 2-propylhept-2-enal;

separating the organic phase from the aqueous phase;

treating the organic phase with hydrogen in the presence of a heterogeneous catalyst to perform a hydrogenation to obtain a third reaction mixture containing at least 2-propyl-1-heptanol; and obtaining a target fraction containing 2-propyl-1-heptanol from the third reaction mixture:

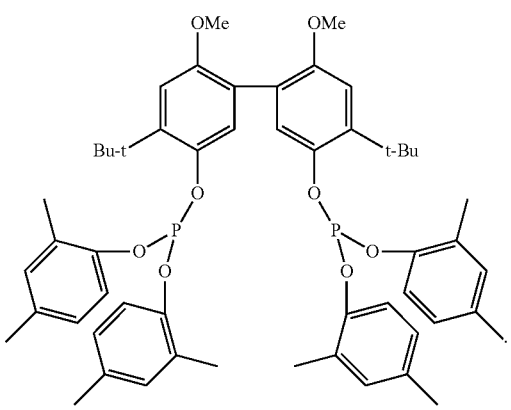

(1)

2. The process of claim 1, wherein the hydroformylation is performed at a temperature between 120° C. and 140° C. and at a pressure between $15*10^5$ Pa and $25*10^5$ Pa.

3. The process of claim 1, wherein
the input mixture further contains a 1-butene,
the cis-2-butene and/or trans-2-butene and the 1-butene contained in the input mixture together form a substrate, and
a regioselectivity for n-pentanal is 96% to 99%.

4. The process of claim 3, which is performed over a period of at least 2000 h,
wherein the regioselectivity for n-pentanal ranges between 96% and 99% over the entire period; except for isolated metrology-dependent outliers.

5. The process of claim 1, wherein the hydroformylation is carried out in the presence of an organic amine of formula (3):

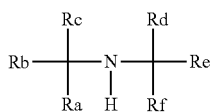

(3)

where Ra, Rb, Rc, Rd, Re and Rf are identical or different hydrocarbyl radicals which are optionally joined to one another.

6. The process of claim 5, wherein the organic amine comprises at least one 2,2,6,6-tetramethylpiperidine unit.

7. The process of claim 6, wherein the organic amine is a di-4-(2,2,6,6-tetramethylpiperidinyl) sebacate.

8. The process of claim 1, wherein the input mixture comprises, relative to 100% by weight of the input mixture:
a total of cis-2-butene and trans-2-butene: 10% by weight to 50% by weight;
1-Butene: 0% to 5% by weight;
a total of n-butane and isobutane: 50% by weight to 90% by weight; and other substances: 0 to 1 wt %.

9. The process of claim 1, wherein
a concentration of rhodium in the first reaction mixture is between 1 ppmw and 1000 ppmw,
a ligand/rhodium ratio is between 1:1 to 100:1, and
no other ligand is provided as part of the homogeneous catalyst system.

* * * * *